United States Patent [19]
Barry et al.

[11] Patent Number: 5,755,722
[45] Date of Patent: May 26, 1998

[54] STENT PLACEMENT DEVICE WITH MEDICATION DISPENSER AND METHOD

[75] Inventors: James J. Barry, Marlboro; Peter M. Nicholas, South Dartmouth; Ronald A. Sahatjian, Lexington, all of Mass.

[73] Assignee: Boston Scientific Corporation, Natick, Mass.

[21] Appl. No.: 361,963

[22] Filed: Dec. 22, 1994

[51] Int. Cl.$^6$ ............................................. A61F 11/00
[52] U.S. Cl. ........................ 606/108; 606/194; 604/101
[58] Field of Search ............................... 604/96, 101, 103, 604/264; 606/108, 192, 194, 195

[56] References Cited

U.S. PATENT DOCUMENTS

| | | | |
|---|---|---|---|
| 4,733,665 | 3/1988 | Palmaz | 606/108 X |
| 4,776,337 | 10/1988 | Palmaz | 604/108 X |
| 5,213,576 | 5/1993 | Abiuso et al. | 604/96 |
| 5,254,089 | 10/1993 | Wang | 604/96 |
| 5,364,356 | 11/1994 | Hofling | 604/96 |
| 5,403,280 | 4/1995 | Wang | 604/96 |
| 5,458,575 | 10/1995 | Wang . | |

*Primary Examiner*—Mark Bockelman

[57] ABSTRACT

An inflatable medical device and method for the placement of a stent in a body passageway by means of a two stage expansion of the stent and for the delivery of medications to precise location in the passageway. The device includes a catheter shaft (14) having a plurality of lumens (13, 22, 28) disposed therein. The catheter shaft has a distal end adapted to be disposed within a vascular passageway. An inflatable balloon is defined by a generally cylindrical wall and is adapted to receive inflation fluids. The balloon is disposed on the distal end of the shaft. An array of circumferentially arranged inflation conduits (40) is disposed in the wall. The conduits (40) are spaced from each other within the wall of the balloon whereby to form a annular array. An array of medication delivering conduits (25) can be disposed within the wall of the balloon. These conduits are adapted to deliver medications to predetermined locations within the body passageway being treated. A stent (30) is removably disposed around the exterior of the wall of the balloon and is expandable radially outwardly from a narrow insertion diameter to a larger second diameter by the expansion of the balloon (16) and then to a still larger third diameter by inflation of the inflation conduits (40) whereby to expand the body passageway and seat the stent.

15 Claims, 2 Drawing Sheets

STENT PLACEMENT DEVICE WITH MEDICATION DISPENSER AND METHOD

BACKGROUND OF THE INVENTION

The present invention relates to a medical device utilizing a balloon catheter for placement of an expandable intraluminal graft, commonly called a stent, within a body passageway such as an artery. Such stents can also be used for the placement of interluminal grafts such as aortic aneurism grafts. The invention especially relates to a medical device including a balloon catheter which can provide forcible expansion of the cross-section of an artery that has been narrowed by atherosclerotic lesion or stenosis and also simultaneously implant a stent at a predetermined site within the artery. The invention further relates to a medical device including a balloon catheter and a method of operating it which can both implant a stent in body passageway and also dispense medication at a predetermined site within the passageway.

DESCRIPTION OF THE PRIOR ART

Devices including balloon catheters for expanding atherosclerotic lesions or stenoses are well known in the art. A device includes an inflatable balloon disposed at the end of multi-lumen catheter shaft in which a pressurizing fluid is forced into the balloon to expand it. The expansion of the balloon engages the surface of the artery to enlarge its cross-section. Balloon use for implantation of stents is also well known to the art. With balloon implantation, the stent is placed on the balloon and the stent is located at a site the physician has decided to treat while viewing the procedure through X-rays. When in the correct location the balloon is deflated and withdrawn leaving the stent behind. A second balloon of larger diameter is placed inside the stent and the second balloon is expanded with a pressurizing fluid to a greater diameter and the stent expands further to engage the portion of the vessel being treated. With such procedures, location of the stent within the vessel is difficult because it requires two balloons and it is difficult to move the stent small distances to precisely locate it. On the other hand, using a large diameter balloon and partially inflating it for locating and then further enlarging it for implantation requires a large profile (diameter) balloon and does not afford the same type of positive engagement between the exterior of the balloon and the stent to enable the physician to make fine adjustments in positioning.

Additionally it is well known to dispense medications from medical balloons. Medical balloons having conduits disposed within their walls and with perforations or openings in the conduits have been disclosed to the prior art. The U.S. Pat. No. 5,254,089 to Wang, and pending divisional application of Wang, Ser. No. 08/088,327, filed Jul. 7, 1993, (and assigned to the same assignee as the present application) disclose a balloon catheter having a multiplicity of medication dispensing perforated conduits disposed within the wall of the balloon.

Stents such as disclosed in the U.S. Pat. No. 4,733,665 to Palmaz, can be disposed about the balloon in the medical device of the present invention. A stent is a tubular-shaped device that can be formed of a plurality of intersecting elongate members. The stent used herein is an interwoven plexus of at least two sets of helically disposed wires wound together with one set juxtaposed relative to the other set to form a tubular arrangement expandable to a plurality of diameters. The device has a first diameter for interluminal delivery into a body passageway. It has a second expanded diameter for application (from the interior) of a radially outwardly extending force such as delivered by a balloon. The second diameter of the stent is variable and dependent upon the amount of force applied to urge it outwardly to expand the lumen of the body passageway. The stent also has a third diameter for implantation, again by internal force, within the passageway. In the prior art, although the balloon is expandable into more than one diameter and the stent is similarly expandable to more than one diameter, usually two balloons are used for the procedure, one for delivery and a larger one for implantation because a balloon large enough for implantation presents a profile that is wider than necessary for the procedure.

SUMMARY OF THE INVENTION

According to the present invention we have discovered an inflatable medical device for placement of a stent in a body passageway by means of a two-stage expansion of the stent on a single balloon. We have also discovered a method of inflating the balloon and implanting the stent. The device includes a catheter shaft with at least two fluid handling lumens and a hollow inflatable balloon having a generally cylindrical wall on the end of the catheter shaft. The interior of the balloon is in fluid flow relation with one of the lumens to provide the interior of the balloon with an inflation fluid. An array of circumferentially arranged inflation conduits is disposed within the wall of the balloon. These conduits are individually segmented and spaced from each other. Their interiors are in fluid flow relation with another of the lumens in the shaft to provide them with inflation fluid but usually are not in fluid flow relation with each other. A stent is disposed around the exterior of the wall of the balloon. The stent is expandable radially outwardly from a narrow insertion diameter to a larger second diameter by expansion of the balloon and then to a larger third diameter by inflation of the inflation conduits to expand the stent within the body passageway and implant it.

In a further embodiment of the present invention, one of the lumens of the two-inflation-lumen catheter shaft is used for dispensing medications from the conduits within the wall of the balloon. The conduits are in fluid flow connection with the inflation lumen to dispense medications and also to inflate them. Thus the device of the present invention enables not only the insertion and implantation of the stent but also the precise placement of medications within the portion of the body passageway being treated.

To make the catheter of the present invention two dissimilar polymeric materials are co-extruded. One of the extrusions forms a tube and the other extrusion (disposed as discrete segments within wall of the tube) forms a circumferentially arranged array of strands. The polymers we have found useful are polyethylene terephthalate for the tube and polyethylene for the strands. The strands are withdrawn from the tube to form conduits. The tube is then expanded and the conduits are expanded also. Some, but not necessarily all, of the conduits can be perforated to form medication dispensing conduits leaving the unperforated conduits as inflation conduits. The balloon and the conduits are conventionally attached to a catheter shaft with lumens in fluid flow communication with inflatable portions of the balloon. The balloon is then wrapped conventionally and the stent, in its narrowest diameter, is placed around the wrapped balloon.

After insertion to approximately the correct location, the balloon on the catheter shaft is inflated to a first diameter through one of the inflation lumens to expand the stent to a first diameter and enable positioning of the stent and forcible expansion of the cross-section of the body passageway. The balloon is then expanded to a still larger diameter by forcing inflation fluid through another of the inflation lumens to inflate the inflation conduits thereby expanding the stent to an still larger diameter to enable seating and implantation of the stent within the body passageway. In a further embodiment, medications can be dispensed through perforations in some of the conduits disposed within the wall of the balloon. In either embodiment after implantation of the stent and the introduction of medications the balloon is withdrawn from within the stent which is now seated within the body passageway.

DESCRIPTION OF THE PREFERRED EMBODIMENTS

Figure 1:
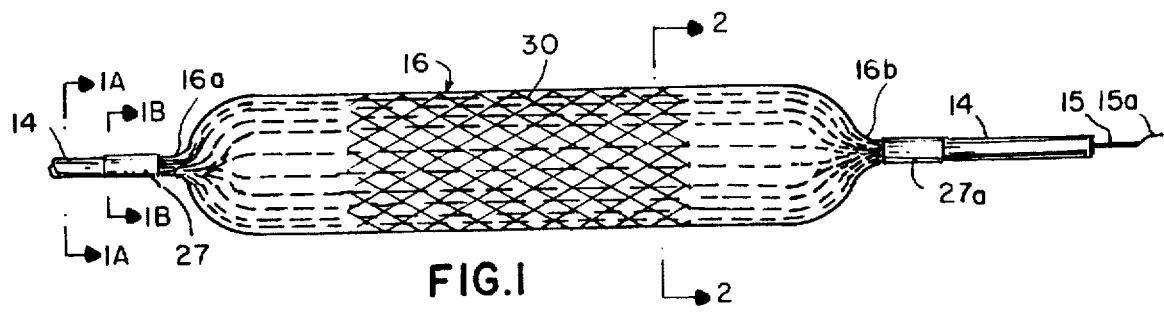
FIG. 1 is a side elevational view of an expanded medical balloon with an expanded stent disposed upon it.

Referring to the drawings, a balloon-type medical catheter is shown. The balloon-type catheter of the present invention is similar to other catheters used for treating coronary artery disease except as otherwise shown and described. As is conventional, the catheter utilizes sleeves 27 and 27a to connect the balloon 16 to the catheter shaft 14. The sleeve 27 is utilized for the transfer of inflation fluids and medications from lumens in the multiluminal tubing forming catheter shaft 14 to a medical balloon 16. The balloon 16 is disposed at the distal end of the catheter shaft 14. Medical balloon 16 is made of materials described herein and is heat-sealed or adhesively attached at its respective ends 16a and 16b to catheter shaft 14.

Figure 1A:
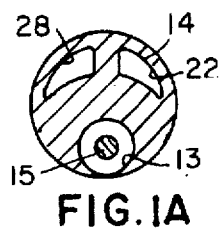
FIGS. 1A and 1B are sectional views taken along the lines 1A—1A and 1B—1B respectively showing lumens of the catheter shaft and the attachment between the catheter shaft and the balloon.
Figure 1B:
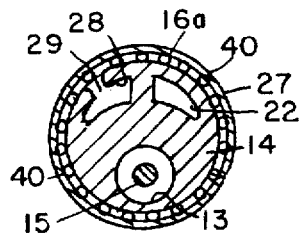
Figure 2:
FIG. 2 is a side view of the balloon according to the present invention in a deflated and wrapped state and with a collapsed stent disposed about it.

As shown in FIGS. 1A and 1B, inflation lumens 22 and 28 are disposed within the catheter shaft 14. One of these inflation lumens is used to inflate the balloon 16 and the other is used to inflate the individual balloons constituting the array of circumferentially arranged inflation conduits 40. As shown in FIG. 2A, port 20 provides communication between the interior of the balloon 16 and the lumen 22. Similarly with regard to inflation lumen 28 a port (not shown) is cut in the inflation lumen 28 and disposed within the sleeve 27 to provide communication between inflation lumen 28 and the array of conduits 40 and 25 (shown in FIG. 2B and 2D). Lumen 28 extends through the catheter shaft 14 and communicates with a fluid introduction port (not shown) at the proximal end of the shaft 14.

Medications in fluid form can also be introduced through lumen 28 provided within the catheter shaft 14 through the fluid introduction port (not shown) at the proximal end of the catheter shaft 14. The medication conduits 25 can have perforations 21 disposed in the walls thereof. A third lumen 13 extends completely through the catheter shaft 14 so a conventional guidewire 15 having a conventional exploratory tip 15a may be inserted in balloon 13 to assist catheter insertion in a body passageway in a conventional manner.

In the preferred embodiments, the conduits 25 and 40 are circumferentially arranged within the perimeter of wall of balloon 16. Each of the medication-dispensing conduits 25 is provided with one or more perforations 21 to enable entry of medications into the body passageway that has been catheterized. In some embodiments these perforations 21 can be helically-arranged around the perimeter of balloon 16 but any configuration that allows the introduction of medications can be used. In other embodiments, there are no perforations over the length of the medication dispensing conduits 25 but rather the conduits 25 terminate in apertures at their distal ends for dispensing the medications. The perforations 21 are formed in the conduits 25 by inflating both the balloon 16 and the conduits 25 and then pricking each conduit wall lightly with a pin until it deflates. Alternatively, conduits 25 can be pierced with laser irradiation. The perforations 21 preferably have diameters in the range 0.0001 to 2.5 mm, depending upon the viscosity of the medication being dispensed, the desired flow rate and the conduit diameter. On the other hand elongated slits on the outside of the conduits can be used also, if required for the introduction of very viscous material or particulate material. The cross-sectional shape of the conduits 25 is important only to the extent that they can receive the medications being dispensed. Conduits having square or rectangular sectional shapes are easy to make and will provide the necessary dispensing functions.

An array of circumferentially-arranged inflation conduits 40 is also disposed in the wall of the balloon 16. In the shown embodiment each inflation conduit 40 is disposed between two medication dispensing conduits 25 and vice versa but such relationships need not be maintained so long as the inflation conduits 40 can expand the balloon sufficiently to seat the stent 30 in the body passageway. Each of the inflation conduits 40 is in fluid flow relation with the inflation lumen 22 disposed in the shaft 14. Inflation of the balloon 16 through lumen 20 and port 28 causes the balloon 16 to unwrap and form the generally cylindrical configuration shown in FIGS. 1 and 2A. The expansion causes the proximal and distal ends of the balloon 16 to assume a generally conical shape. In the collapsed state, such as shown in FIG. 2, the profile of the balloon 16 can approximate the diameter of the shaft 14 because extremely thin-walled balloons can be employed, as will be described hereinafter.

Figure 2A:
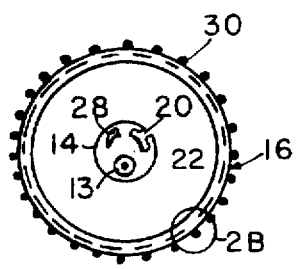
FIGS. 2A and 2B are cross-sectional views taken along the line 2—2 of FIG. 1. In these views the balloon is expanded and the stent disposed about it is expanded also.
Figure 2C:
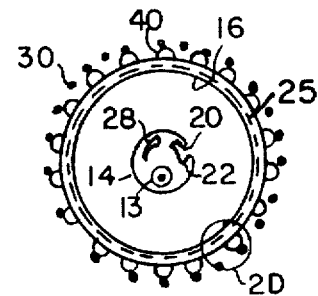
FIGS. 2C and 2D are views similar to the views of FIGS. 2A and 2B except in these views the inflation conduits are inflated also to fully expand the stent disposed around the balloon catheter for implantation. Uninflated conduits are used for dispensing medications.
Figure 2B:
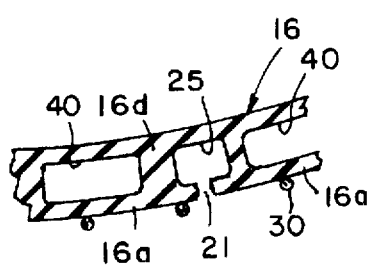
Figure 2D:
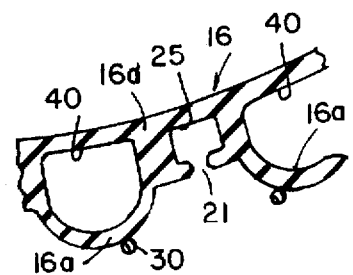

In FIGS. 1, 2A and 2C the balloon 16 is shown in an inflated state. Each of the medication dispensing conduits 25 and the inflation conduits 40 are shown to share a common side wall 16d. The wall thicknesses of each wall can be between about 0.0001 and 0.004 inches with 0.003 to 0.002 inches being preferred. The deflated profile of the balloon 16 can be 0.003 inches or less. The interior of the balloon, that is the inner diameter of the balloon, can be between about 0.02 and 2.0 inches. The inflation conduits 40 can have widths of between about 0.25 and 2.0 mm. Inflation conduits 40, as shown in FIG. 2D can double and even triple in width thus providing a significant increase in the diameter of the stent 30 that is disposed about it as will be discussed hereinafter. Generally there should be between about 6 and 48 inflation conduits arranged circumferentially within the wall of the balloon.

A stent that has proven useful with the balloon catheter of the present invention is a tubular-shaped member having first and second ends and a wall surface disposed between the first and second ends. The wall surface is formed of a plurality of intersecting elongate members some of which intersect with one another intermediate the first and second ends of the tubular member. The tubular-shaped member has a first diameter which permits delivery of the member into a body passageway. The tubular member has a second, expanded diameter which is formed upon the application from the interior of the tubular-shaped member of a radially outwardly extending force. The second diameter is variable and depends upon the amount of force applied to the tubular-shaped member so that the member can be expanded at an intraluminal site proposed for implantation. The tubular member also has a third diameter which is larger than the first and second diameters. The third diameter is used for the actual intraluminal implantation of the stent 30. Preferably the stent 30 is formed of a plurality of wires with the wires fixedly secured to one another where they intersect each other. On the other hand the elongated members may be a plurality of thin bars which are also fixedly secured to one another where they intersect. Although metal is most frequently used for the stent, polymeric materials formed in similar shapes can also be used. Polymeric materials have the advantage that certain compositions, as is well known, can be absorbed by the body so that after the stenosis is remedied they can disappear.

As can be seen in FIG. 2, the stent 30 closely engages the balloon 16 when it is wrapped. When the balloon 16 is inflated (as shown in FIGS. 1 and 2A) the stent 30 will expand due to the radially outwardly extending force of the balloon. The individual members forming the stent 30 will space themselves further apart. The stent 30, although expanded, can still be moved within the body passageway in which it is inserted. As a benefit this can allow the stent 30 to be moved back and forth for precise location. When the location is correct, the inflation conduits 40 are inflated and the diameter of the device will be enlarged further thereby enlarging the diameter of the stent 30 which surrounds it. The stent is then permanently implanted within the body passageway being treated.

Following the permanent seating of the stent the balloon and the inflation conduits are deflated. The balloon 16 is withdrawn from within the stent and the catheter is removed from the body passageway. With the balloon of the present invention a 6 mm balloon (inflated diameter) can expand to 6.5 or 7.0 mm to expand the stent. In addition with the medication delivery conduits disposed within the wall of the balloon the physician can even change medications from one used for preimplantation to a different one for post-implantation medication as desired.

It is apparent that changes and modifications can be made within the spirit and scope of the present invention, it is our intention, however, only to be limited by the scope of the appended claims.

As our invention we claim:

1. An inflatable medical device for the placement of a stent in a body passageway by means of a two-stage expansion of said stent, said device comprising:

a catheter shaft (14) having at least two lumens (13, 22 or 28) disposed therein, said catheter shaft having a distal end adapted to be disposed within said body passageway;

a hollow, inflatable, balloon (16) defined by a generally cylindrical wall and having a proximal end, the proximal end of the balloon being disposed on the distal end of said catheter shaft, the interior of said balloon being in fluid flow relationship with a first of said lumens whereby to provide the interior of said balloon with an inflation fluid;

an array of circumferentially arranged inflation conduits (40) disposed in said wall, said conduits (40) being spaced from each other within said wall whereby to form an annular array, the interior of said conduits being in fluid flow relationship with a second of said lumens whereby to provide said conduits with an inflation fluid;

a stent (30) removably disposed around the exterior of the wall of said balloon, said stent being expandable radially outwardly from a narrow insertion diameter to a larger second diameter by the expansion of said balloon and then to a still larger third diameter by inflation of said inflation conduits whereby to expand said body passageway and seat said stent.

2. The medical device according to claim 1 wherein said inflation conduits (40) are uniformly arrayed and spaced from each other around said balloon (16).

3. The medical device according to claim 1 wherein the stent is an interwoven plexus of at least two sets of helically disposed wires wound together with one set juxtaposed relative to the other set to form a tubular arrangement expandable to a plurality of diameters.

4. A method of implanting a stent in a vascular passageway, said method comprising:

disposing on a catheter shaft having at least two lumens a hollow, inflatable, balloon (16) defined by a generally cylindrical wall and having a distal and a proximal end, the proximal end of the balloon being disposed on the distal end of said catheter shaft, the interior of said balloon being in fluid flow relationship with a first of said lumens whereby to provide the interior of said balloon with an inflation fluid, said wall further having an array of circumferentially arranged spaced-apart inflation conduits (40) disposed therein, the interior of said conduits being in fluid flow relationship with a second of said lumens whereby to provide said conduits with an inflation fluid;

removably disposing a stent (30) around the exterior of the wall of said balloon, said stent being expandable radially outwardly from a narrow insertion diameter to a larger second diameter by the expansion of said balloon and then to a larger third diameter by inflation of said inflation conduits whereby to expand said body passageway and seat said stent.

5. The method according to claim 4 further including the steps inserting said balloon with said stent within a body passageway to a predetermined location, inflating said balloon to expand the diameter and initially site said stent, inflating said inflation conduits to expand the diameter said stent further and seat said stent in a predetermined location and then withdrawing inflation fluids from both said balloon and said inflation conduits and withdrawing said balloon from said stent.

6. A method of implanting a stent in a body passageway and dispensing medications to a predetermined site, said method comprising:

disposing on a catheter shaft having at least three lumens a hollow, inflatable, balloon (16) defined by a generally cylindrical wall and having a distal and a proximal end, the proximal end of the balloon being disposed on the distal end of said catheter shaft, the interior of said balloon being in fluid flow relationship with a first of said lumens whereby to provide the interior of said balloon with an inflation fluid, said wall further having an array of circumferentially arranged spaced-apart inflation conduits (40) disposed therein, the interior of said inflation conduits being in fluid flow relationship with a second of said lumens whereby to provide said conduits with an inflation fluid, said wall further having an array of circumferentially arranged spaced-apart medication-dispensing conduits disposed therein, the interior of said medication-dispensing conduits being in fluid flow relationship with said second lumen whereby to provide said conduits with a medication;

removably disposing a stent (30) around the exterior of the wall of said balloon, said stent being expandable radially outwardly from a narrow insertion diameter to a larger second diameter by the expansion of said balloon and then to a larger third diameter by inflation of said inflation conduits whereby to expand said body passageway and seat said stent.

7. The method according to claim 6 further including the steps inserting said balloon with said stent within a vascular passageway to a predetermined location, inflating said balloon to expand the diameter and initially site said stent, inflating said inflation conduits to expand the diameter said stent further and seat said stent in a predetermined location, dispensing medications to a predetermined site through said medication-dispensing conduits and then withdrawing inflation fluids from both said balloon and said inflation conduits and withdrawing said balloon from said stent.

8. A method of implanting a stent in a body passageway, said method comprising:

disposing a stent having a first diameter that is expandable in diameter on a medical balloon, said balloon being expandable to a plurality of diameters by separate inflation mechanisms;

inserting said stent and balloon in a body passageway; inflating said balloon to a second diameter with one of the mechanisms, thereby expanding the stent to said second diameter and enabling location of said stent within the body passageway;

inflating said balloon to a still larger third diameter with a second of said mechanisms, thereby expanding the stent to said third diameter and enabling seating of said stent within said body passageway.

9. An inflatable medical device for the placement of a stent in a vascular passageway by means of a two-stage expansion of said stent, said device comprising:

a catheter shaft (14) having at least two lumens (13, 22 or 28) disposed therein, said catheter shaft having a distal end adapted to be disposed within said vascular passageway; a hollow, an inflatable, balloon (16) defined by a generally cylindrical wall and having a proximal end, the proximal end of the balloon being disposed on the distal end of said catheter shaft, the interior of said balloon being in fluid flow relationship with a first of said lumens whereby to provide the interior of said balloon with an inflation fluid;

an array of circumferentially-arranged imperforate inflation conduits (40) disposed within said wall, said conduits (40) being spaced from each other within said wall whereby to form an annular array, the interior of said conduits being in fluid flow relationship with a second of said lumens whereby to provide said conduits with an inflation fluid to inflate said conduits;

a stent (30) removably disposed around the exterior of the wall of said balloon, said stent being expandable radially outwardly from a narrow insertion diameter to a larger second diameter by inflation of said balloon and then to a still larger diameter by inflation of said inflation conduits whereby to expand said vascular passageway and seat said stent.

10. The medical device according to claim 9 wherein said inflation conduits (40) are uniformly arrayed and spaced from each other around said balloon (16).

11. The medical device according to claim 9 wherein the stent is an interwoven plexus of at least two sets of helically-disposed wires wound together with one set juxtaposed relative to the other set to form a tubular arrangement expandable to a plurality of diameters.

12. An inflatable medical device for the placement of a stent in a vascular passageway by means of a two-stage expansion of said stent and for the intravascular delivery of medications, said device comprising:

a catheter shaft (14) having a plurality of lumens (13, 22, 28) disposed therein, said catheter shaft having a distal end adapted to be disposed within a vascular passageway;

an inflatable balloon defined by a generally cylindrical wall and adapted to receive inflation fluids, said balloon being disposed on the distal end of said shaft;

an array of circumferentially-arranged inflation conduits (40) disposed in said wall, said conduits (40) being spaced from each other within the wall of said balloon (16) whereby to form an annular array;

means for delivering an inflation fluid from a first of said lumens in said shaft to said balloon (16) and means for the delivery of an inflation fluid from a second of said lumens to said conduits (25, 40) whereby increases in balloon diameter can be provided in two stages of said balloon and said conduits;

an array of medication-delivering conduits (25) also disposed within the wall of said balloon (16), a third of said lumens (13, 22 or 28) being connected to said medication-delivering conduits (25);

dispensing means disposed on the outer surfaces of said medication-dispensing conduits (25), said medication-dispensing conduits being adapted to deliver medications from said third lumen to predetermined locations within said vascular passageway;

a stent (30) removably disposed around the exterior of the wall of said balloon, said stent being expandable radially outwardly from a narrow insertion diameter to a larger second diameter by the expansion of said balloon and then to a larger third diameter by inflation of said inflation conduits whereby to expand said body passageway and seat said stent.

13. The medical device according to claim 12 wherein said conduits are arranged around said balloon, said conduits being spaced from each other on said balloon and individually segmented from each other.

14. The medical device according to claim 12 wherein said dispensing means includes perforations on said conduits.

15. The medical device according to claim 12 wherein each of said medication dispensing conduits (25) have at least one perforation on their lengths whereby to provide egress for medications from said balloon.

* * * * *